(12) United States Patent
Hwang et al.

(10) Patent No.: US 11,976,039 B2
(45) Date of Patent: May 7, 2024

(54) METHOD OF PRODUCING AROMATIC HYDROCARBONS

(71) Applicant: LG CHEM, LTD., Seoul (KR)

(72) Inventors: Sung June Hwang, Daejeon (KR); Tae Woo Kim, Daejeon (KR); Sung Kyu Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 169 days.

(21) Appl. No.: 17/430,302

(22) PCT Filed: Nov. 9, 2020

(86) PCT No.: PCT/KR2020/015575
§ 371 (c)(1),
(2) Date: Aug. 11, 2021

(87) PCT Pub. No.: WO2021/256623
PCT Pub. Date: Dec. 23, 2021

(65) Prior Publication Data
US 2022/0306555 A1    Sep. 29, 2022

(30) Foreign Application Priority Data

Jun. 16, 2020  (KR) .................. 10-2020-0072891
Oct. 28, 2020  (KR) .................. 10-2020-0141070

(51) Int. Cl.
*C07C 7/167* (2006.01)
*C07C 7/08* (2006.01)
(Continued)

(52) U.S. Cl.
CPC ............ *C07C 7/167* (2013.01); *C07C 7/08* (2013.01); *C07C 15/04* (2013.01); *C07C 15/08* (2013.01); *C07C 15/46* (2013.01)

(58) Field of Classification Search
None
See application file for complete search history.

(56) References Cited

U.S. PATENT DOCUMENTS 3,684,665 A * 8/1972 Abe .................. C10G 7/08
203/64
4,097,371 A    6/1978 Giroux
(Continued)

FOREIGN PATENT DOCUMENTS

CN    101208409 A    6/2008
CN    102348784 A    2/2012
(Continued)

*Primary Examiner* — In Suk C Bullock
*Assistant Examiner* — Alyssa L Cepluch
(74) *Attorney, Agent, or Firm* — Bryan Cave Leighton Paisner LLP

(57) ABSTRACT

Method of producing aromatic hydrocarbons including: supplying a raw material stream to a C6 separation column, supplying an upper discharge stream from the C6 separation column to a first gasoline hydrogenation unit, and supplying a lower discharge stream from the C6 separation column to a C7 separation column; supplying an upper discharge stream from the C7 separation column to a hydrodealkylation reaction unit and supplying a lower discharge stream from the C7 separation column to a C8 separation column; separating benzene from discharged streams from the first gasoline hydrogenation unit and the hydrodealkylation reaction unit; removing a lower discharge stream from the C8 separation column and supplying an upper discharge stream from the C8 separation column to a second extractive distillation column; and separating styrene from a lower discharge stream of the second extractive distillation column and separating xylene from an upper discharge stream of the second extractive distillation column.

6 Claims, 3 Drawing Sheets

(51) Int. Cl.
    *C07C 15/04*     (2006.01)
    *C07C 15/08*     (2006.01)
    *C07C 15/46*     (2006.01)

(56) References Cited

U.S. PATENT DOCUMENTS

| | | | |
|---|---|---|---|
| 5,573,645 A * | 11/1996 | Pickering, Jr. | C07C 7/04 203/25 |
| 5,685,972 A | 11/1997 | Timken et al. | |
| 2003/0092952 A1 * | 5/2003 | Netzer | C10G 69/12 585/648 |
| 2010/0228063 A1 * | 9/2010 | Almering | C07C 15/04 585/266 |
| 2012/0067776 A1 | 3/2012 | Diehl et al. | |

FOREIGN PATENT DOCUMENTS

| | | |
|---|---|---|
| CN | 105316040 A | 2/2016 |
| EP | 0893487 A1 | 1/1999 |
| JP | 2008-543893 A | 12/2008 |
| JP | 2010-047484 A | 3/2010 |
| JP | 2012-509976 A | 4/2012 |
| KR | 10-0645659 B1 | 11/2006 |
| KR | 10-2007-0068254 A | 6/2007 |
| KR | 10-0894400 B1 | 4/2009 |
| KR | 1020120013946 A | 2/2012 |
| KR | 10-2016-0025512 A | 3/2016 |

* cited by examiner

[FIG. 1]
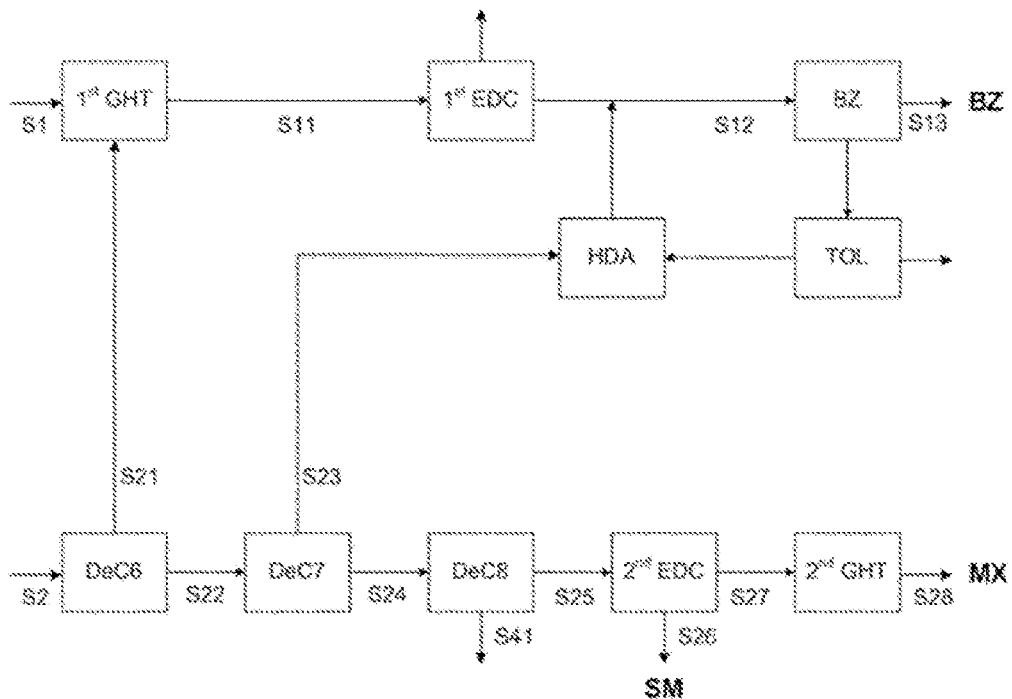
[FIG. 2]
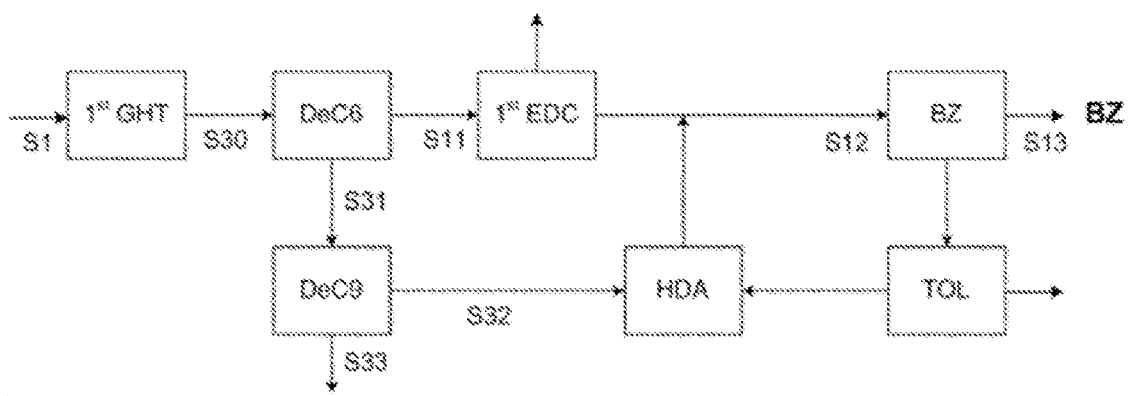

[FIG. 3]
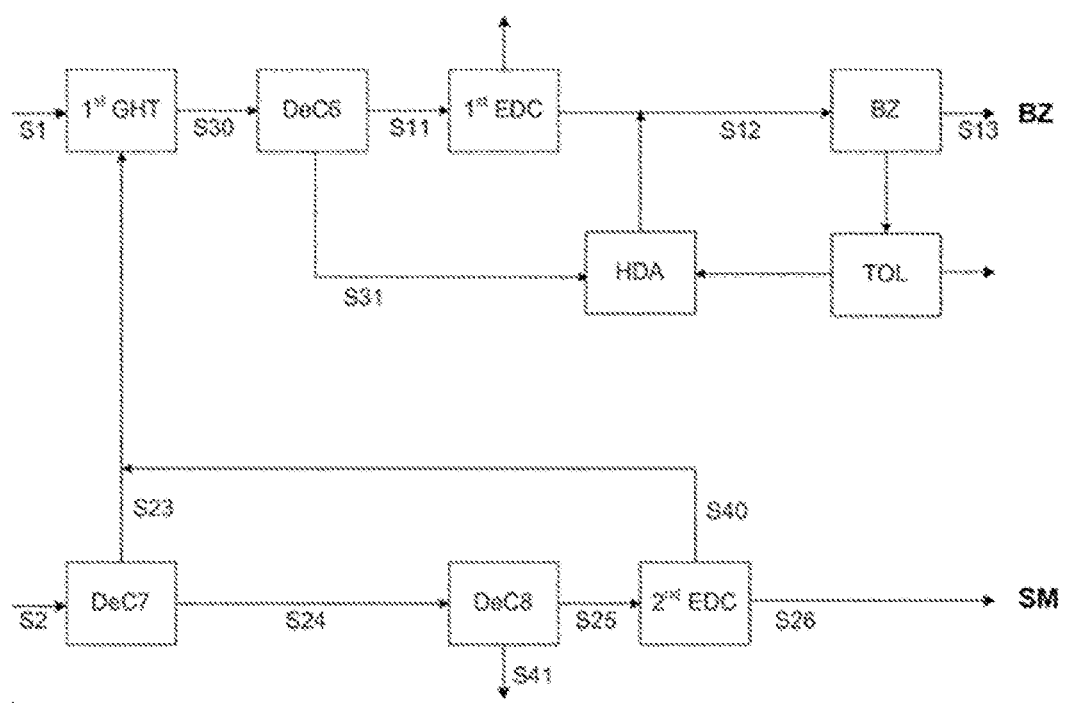

[FIG. 4]
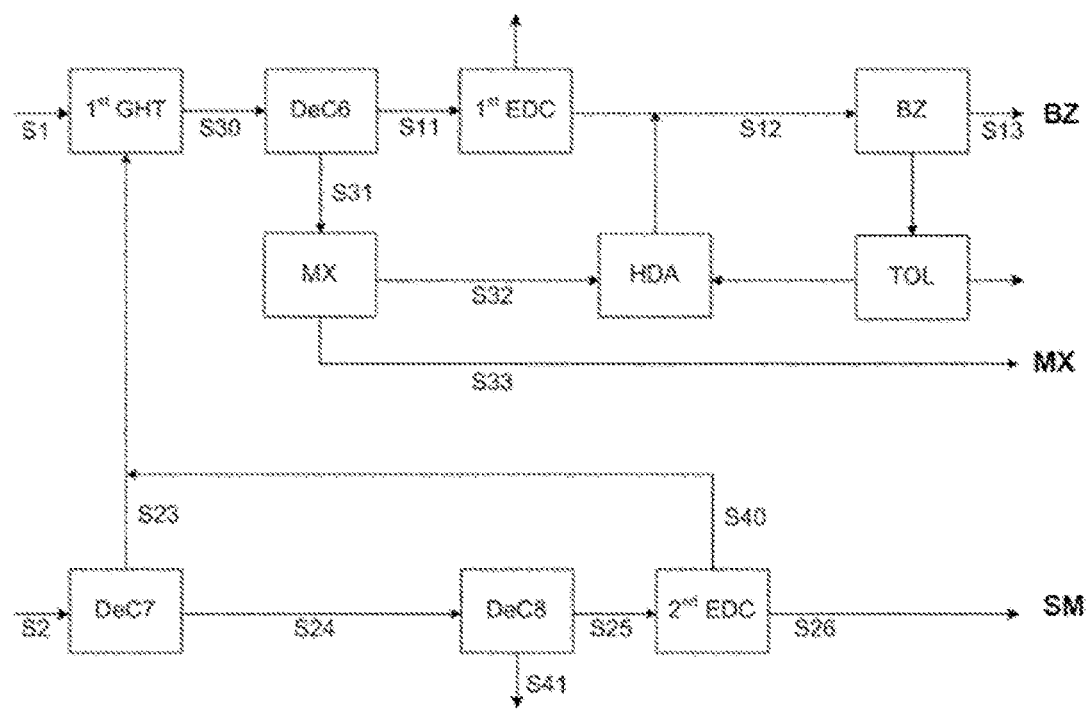

METHOD OF PRODUCING AROMATIC HYDROCARBONS

CROSS-REFERENCE TO RELATED APPLICATIONS

This application is a U.S. national stage of international application No. PCT/KR2020/015575, filed on Nov. 9, 2020, and claims the benefit of priority to Korean Patent Application No. 10-2020-0072891 filed on Jun. 16, 2020, and Korean Patent Application No. 10-2020-0141070 filed on Oct. 28, 2020, the entire contents of which are incorporated herein as a part of the specification.

TECHNICAL FIELD

The present invention relates to a method of producing aromatic hydrocarbons, and more particularly, to a method of producing benzene, xylene, and styrene simultaneously in a single process.

BACKGROUND

A naphtha cracking center (hereinafter, referred to as "NCC") is a process of pyrolyzing naphtha which is a fraction of gasoline at a temperature of about 950° C. to 1,050° C. to produce ethylene, propylene, butylene, and benzene, toluene, and xylene (BTX), and the like which are basic raw materials of petrochemical products.

Conventionally, raw pyrolysis gasoline (RPG), which is a by-product of a process of producing ethylene and propylene using the naphtha as a raw material, was used to produce benzene and styrene in separate processes.

The process of producing benzene was performed by largely including a gasoline hydrogenation (GHT, hydrodesulfurization) process, a prefraction (PF) process, an extractive distillation process (EDP), and a hydrodealkylation (HDA, dealkylation) process using an RPG raw material stream. In this case, the raw material is supplied to the gasoline hydrogenation (GHT) process without separating C7+ hydrocarbons from a raw material stream, thereby increasing an amount of hydrogen used due to an increase in a flow rate supplied to the gasoline hydrogenation (GHT) process. In addition, after the gasoline hydrogenation (GHT) process, a C6 hydrocarbon and C7+ hydrocarbons are separated, and the C7+ hydrocarbons are subjected to hydrodealkylation again and then mixed again to separate benzene, and thus, energy is doubly consumed.

In addition, the styrene extractive distillation process is a process of directly producing styrene from RPG through an extractive distillation process (EDP), and may be positioned at a front end of a benzene production process. Here, a prefraction (PF) process step of RPG to C7− hydrocarbons, a C8 hydrocarbon, and C9+ hydrocarbons is performed beforehand to separate a C8 hydrocarbon abundant in styrene before supplying the RPG to EDP. However, in this case, because the separated C7− hydrocarbons and C8 hydrocarbon are introduced into the benzene production process and subjected to a gasoline hydrogenation (GHT) process step, they are mixed again. After performing the GHT step, the C7− hydrocarbons and the C8 hydrocarbon are separated again in the benzene production process, and as such, performing a step of separating C7− hydrocarbons and a C8 hydrocarbon twice leads to a waste of process costs and energy.

SUMMARY

To solve these problems, an objective of the present invention is to provide a method which produces benzene, xylene, and styrene simultaneously in a single process, while simplifying the process and reducing energy.

In one exemplary embodiment, a method of producing aromatic hydrocarbons includes: a step of supplying a raw material stream to a C6 separation column, supplying an upper discharge stream from the C6 separation column to a first gasoline hydrogenation unit, and supplying a lower discharge stream from the C6 separation column to a C7 separation column; a step of supplying an upper discharge stream from the C7 separation column to a hydrodealkylation reaction unit and supplying a lower discharge stream from the C7 separation column to a C8 separation column; a step of separating benzene from a discharge stream from the first gasoline hydrogenation unit and a discharge stream from the hydrodealkylation reaction unit; a step of removing a lower discharge stream from the C8 separation column and supplying an upper discharge stream from the C8 separation column to a second extractive distillation column; and a step of separating styrene from a lower discharge stream from the second extractive distillation column and separating xylene from an upper discharge stream from the second extractive distillation column.

According to the exemplary method of producing aromatic hydrocarbons of the present invention, benzene, xylene, and styrene may be produced simultaneously in a single process. In this process, a prefraction process step which was required in production of benzene may be omitted to simplify the process and reduce energy due to a decrease in an amount of steam used.

In addition, only a C6− hydrocarbon stream excluding C7+ hydrocarbons in the raw material stream is supplied to a first gasoline hydrogenation unit, thereby decreasing a flow rate supplied to the first gasoline hydrogenation unit to decrease an amount of hydrogen used in the first gasoline hydrogenation unit and increasing a catalyst lifetime.

In addition, a second gasoline hydrogenation unit is installed, and an upper discharge stream from a second extractive distillation column may be supplied to a second gasoline hydrogenation unit to further produce xylene, without needing a complicated process of supplying the upper discharge stream from the second extractive distillation column to the first gasoline hydrogenation unit, performing a prefraction process, performing a dealkylation reaction to perform conversion into benzene, and then separating benzene.

In addition, a C6 separation column is installed at a front end of a C7 separation column and a raw material stream is supplied to the C6 separation column, thereby separating C6− hydrocarbons and a C7 hydrocarbon, respectively, supplying the C6− hydrocarbons to the first gasoline hydrogenation unit, and supplying the C7 hydrocarbon to the hydrodealkylation reaction unit. Thus, columns for prefraction in a rear end of the first gasoline hydrogenation unit may be removed.

BRIEF DESCRIPTION OF DRAWINGS

FIG. 1 is a process flow chart of a method of producing aromatic hydrocarbons according to Examples 1 and 2 of the present invention.

FIG. 2 is a process flow chart of a method of producing aromatic hydrocarbons according to Comparative Example 1.

FIG. 3 is a process flow chart of a method of producing aromatic hydrocarbons according to Comparative Example 2.

FIG. 4 is a process flow chart of a method of producing aromatic hydrocarbons according to Comparative Example 3.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the terms in order to describe their own inventions in the best mode.

In the present invention, the term "stream" may refer to a fluid flow in a process, or may refer to a fluid itself flowing in a pipe. Specifically, the "stream" may refer to both a fluid itself flowing in a pipe connecting each apparatus and a fluid flow. In addition, the fluid may refer to a gas or a liquid.

In the present invention the term "C# hydrocarbon", wherein "#" is a positive integer, represents all hydrocarbons having # carbon atoms. Therefore, the term "C8 hydrocarbon" represents a hydrocarbon compound having 8 carbon atoms. In addition, the term "C#+ hydrocarbon" represents all hydrocarbon molecules having # or more carbon atoms. Therefore, the term "C9+ hydrocarbon" represents a mixture of hydrocarbons having 9 or more carbon atoms. In addition, the term "C#− hydrocarbon" represents all hydrocarbon molecules having # or fewer carbon atoms. Therefore, the term "C7− hydrocarbon" represents a mixture of hydrocarbons having 7 or fewer carbon atoms.

In the present invention, xylene may include ethylene benzene, m-xylene, o-xylene, and p-xylene.

Hereinafter, the present invention will be described in more detail for better understanding of the present invention.

According to the present invention, a method of producing aromatic hydrocarbons is provided. The method of producing aromatic hydrocarbons produces benzene, xylene, and styrene simultaneously in a single process, and the process may be simplified and process energy may be reduced as compared with the conventional case of producing benzene and styrene in each plant.

Specifically, the conventional process of producing benzene was performed by largely including a gasoline hydrogenation (GHT) process, a prefraction (PF) process, an extractive distillation process (EDP), and a hydrodealkylation (HDA) process using an RPG raw material stream. In this case, the raw material is supplied to gasoline hydrogenation (GHT) without separating C7+ hydrocarbons from a raw material stream, thereby increasing an amount of hydrogen used due to an increase in a flow rate supplied to the gasoline hydrogenation (GHT) process. In addition, after the gasoline hydrogenation (GHT) process, a C6 hydrocarbon and C7+ hydrocarbons are separated, and the C7+ hydrocarbons are subjected to hydrodealkylation again and then mixed again to separate benzene, and thus, energy is doubly consumed.

In addition, the styrene extractive distillation process is a process of directly producing styrene from RPG through an extractive distillation process (EDP), and may be positioned at a front end of a benzene production process. A prefraction (PF) process step of converting RPG to C7− hydrocarbons, a C8 hydrocarbon, and C9+ hydrocarbons is performed to separate a C8 hydrocarbon before supplying the RPG to EDP. However, since the separated C7− hydrocarbons and C8 hydrocarbon are be introduced into the benzene production process and subjected to a gasoline hydrogenation (GHT) process step, they are mixed again. After performing the GHT step, the C7− hydrocarbons and the C8 hydrocarbon are separated again in the benzene production process, and as such, performing a step of separating C7− hydrocarbons and a C8 hydrocarbon twice leads to a waste of process costs and energy.

Conventionally, RPG was used to produce benzene and styrene in separate processes. In this case, there were problems of unnecessary process steps and excessive energy consumption as described above.

To address these deficiencies, in the present invention, a process capable of producing benzene, styrene, and also xylene simultaneously, which may not be technically derived from each conventional process for producing benzene and styrene, was designed, and the process was further simplified and the amount of benzene, xylene, and styrene relative to an amount of a raw material used was maximized while minimizing a process energy use.

According to an exemplary embodiment of the present invention, the method of producing aromatic hydrocarbons may be described with reference to FIG. 1. As illustrated in FIG. 1, a method of producing aromatic hydrocarbons includes: a step of supplying a raw material stream to a C6 separation column (DeC6), supplying an upper discharge stream from the C6 separation column (DeC6) to a first gasoline hydrogenation unit ($1^{st}$ GHT), and supplying a lower discharge stream from the C6 separation column to a C7 separation column (DeC7); a step of supplying an upper discharge stream from the C7 separation column (DeC7) to a hydrodealkylation reaction unit (HDA) and supplying a lower discharge stream from the C7 separation column to a C8 separation column (DeC8); a step of separating benzene from a discharge stream from the first gasoline hydrogenation unit ($1^{st}$ GHT) and a discharge stream from the hydrodealkylation reaction unit (HDA); a step of removing a lower discharge stream from the C8 separation column (DeC8) and supplying an upper discharge stream from the C8 separation column to a second extractive distillation column ($2^{nd}$ EDC); and a step of separating styrene from a lower discharge stream from the second extractive distillation column ($2^{nd}$ EDC) and separating xylene from an upper discharge stream from the second extractive distillation column.

According to an exemplary embodiment of the present invention, the raw material stream may include raw pyrolysis gasoline (RPG). The raw pyrolysis gasoline may be a by-product of a process producing ethylene, propylene, and the like using naphtha in a unit forming a naphtha cracking center (NCC). The RPG as the raw material stream may be a C5+ hydrocarbon mixture, specifically a mixture abundant in C5 to C10 hydrocarbons. For example, the RPG may include one or more selected from the group consisting of iso-pentane, n-pentane, 1,4-pentadiene, dimethyl acetylene, 1-pentene, 3-methyl-1-butene, 2-methyl-1-butene, 2-methyl-2-butene, isoprene, trans-2-pentene, cis-2-pentene, trans-1,3-pentadiene, cyclopentadiene, cyclopentane, cyclopentene, n-hexane, cyclohexane, 1,3-cyclohexadiene, n-heptane, 2-methylhexane, 3-methylhexane, n-octane, n-nonane, benzene, toluene, ethylbenzene, m-xylene, o-xylene, p-xylene, styrene, dicyclopentadiene, indene, and indane.

According to an exemplary embodiment of the present invention, the raw material stream may be first separated into C6− hydrocarbons, a C7 hydrocarbon, and C8+ hydrocarbons to efficiently produce xylene as well as benzene and styrene from the raw material stream including C5 to C10 hydrocarbons. Here, the stream including C6-hydrocarbons and the stream including a C7 hydrocarbon may be streams for producing benzene, and the stream including C8+ hydrocarbons may be a stream for producing styrene and xylene.

According to an exemplary embodiment of the present invention, a C6 separation column (DeC6) and a C7 separation column (DeC7) may be provided to separate the raw material stream into C6− hydrocarbons, a C7 hydrocarbon, and C8+ hydrocarbons. Specifically, the raw material stream was supplied to the C6 separation column (DeC6), an upper discharge stream including C6− hydrocarbons in the C6 separation column (DeC6) was supplied to the first gasoline hydrogenation unit ($1^{st}$ GHT), and a lower discharge stream including C7+ hydrocarbons was supplied to the C7 separation column (DeC7). In addition, in the C7 separation column (DeC7), an upper discharge stream including a C7 hydrocarbon and a lower discharge stream including C8+ hydrocarbons were separated, the upper discharge stream including a C7 hydrocarbon was supplied to the hydrodealkylation reaction unit (HDA), and the lower discharge stream including C8+ hydrocarbons was supplied to a C8 separation column (DeC8).

Consequently, the raw material stream may be separated into a stream including C6− hydrocarbons, a stream including a C7 hydrocarbon, and a stream including C8+ hydrocarbons by passing through the C6 separation column (DeC6) and the C7 separation column (DeC7), and the stream including C6− hydrocarbons may be supplied to the first gasoline hydrogenation unit ($1^{st}$ GHT) to produce benzene, the stream including a C7 hydrocarbon may pass through the hydrodealkylation reaction unit (HDA) to produce benzene, and the stream including C8+ hydrocarbons may be supplied to the C8 separation column (DeC8) to produce styrene and xylene.

In addition, as the C6 separation column (DeC6), a C6 separation column (DeC6) used in the prefraction step in the conventional BTX production process may be reused.

According to an exemplary embodiment of the present invention, the upper discharge stream from the C6 separation column (DeC6) may be supplied to the first gasoline hydrogenation unit ($1^{st}$ GHT) and subjected to a hydrodesulfurization process step of performing hydrodesulfurization in the presence of separately supplied hydrogen and catalyst. The catalyst may be a catalyst allowing selective hydrogenation. For example, the catalyst may include one or more selected from the group consisting of palladium, platinum, copper, and nickel. In some cases, the catalyst may be supported on one or more supporters selected from the group consisting of gamma alumina, activated carbon, and zeolite and then used.

According to an exemplary embodiment of the present invention, benzene may be separated and produced from the discharge stream from the first gasoline hydrogenation unit ($1^{st}$ GHT). Specifically, the discharge stream from the first gasoline hydrogenation unit ($1^{st}$ GHT) is supplied to the first extractive distillation column ($1^{st}$ EDC), and benzene may be separated from the lower discharge stream of the first extractive distillation column ($1^{st}$ EDC).

More specifically, the first gasoline hydrogenation unit ($1^{st}$ GHT) may include the first gasoline hydrogenation reactor and the second gasoline hydrogenation reactor, the upper discharge stream from the C6 separation column (DeC6) is supplied to the first gasoline hydrogenation reactor, the discharge stream from the first gasoline hydrogenation reactor is supplied to the second gasoline hydrogenation reactor, the discharge stream from the second gasoline hydrogenation reactor is supplied to the first extractive distillation column ($1^{st}$ EDC), and benzene may be separated from the lower discharge stream of the first extractive distillation column ($1^{st}$ EDC). Here, the discharge stream from the second gasoline hydrogenation reactor may be passed through a stripper and then supplied to the first extractive distillation column ($1^{st}$ EDC).

In addition, the first gasoline hydrogenation unit ($1^{st}$ GHT) may further include a separately required device in addition to the first gasoline hydrogenation reactor and the second gasoline hydrogenation reactor. For example, the first gasoline hydrogenation unit ($1^{st}$ GHT) may further include a C5 separation column and the C5 separation column may be disposed between the first gasoline hydrogenation reactor and the second gasoline hydrogenation reactor. Thus, the upper discharge stream from the C6 separation column (DeC6) passes through the first gasoline hydrogenation unit ($1^{st}$ GHT), while impurities such as a fuel gas (F/G) and a C5 hydrocarbon may be removed from the upper discharge stream from the C6 separation column (DeC6).

An operation temperature of the first gasoline hydrogenation reactor may be 50° C. to 200° C., 60° C. to 170° C., or 60° C. to 140° C. The first gasoline hydrogenation reactor is operated at a temperature in the above ranges, thereby performing the hydrogenation reaction in a liquid phase. Specifically, in the first gasoline hydrogenation reactor, the hydrogenation reaction may be performed in a liquid phase at a low temperature for removing olefins. For example, the olefin is a hydrocarbon having a double bond, and may include styrene and diolefin. The double bond of the olefin is broken due to the hydrogenation reaction in the first gasoline hydrogenation reactor, so that the olefin may be converted into a saturated hydrocarbon.

An operation temperature of the second gasoline hydrogenation reactor may be 250° C. to 400° C., 280° C. to 360° C., or 280° C. to 320° C. The second gasoline hydrogenation reactor is operated at a temperature in the above ranges, thereby performing the hydrogenation reaction in a gas phase. Specifically, in the second gasoline hydrogenation reactor, residual olefins which have not been removed in the first gasoline hydrogenation reactor are removed and the hydrogenation reaction may be performed in a gas phase for removing sulfur. Thus, the discharge stream from the second gasoline hydrogenation reactor from which olefins and sulfur have been removed may be passed through a stripper without additional prefraction and then supplied to the first extractive distillation column ($1^{st}$ EDC) in a total amount.

Specifically, in the conventional benzene production process, a total amount of the raw material stream is subjected to a hydrodesulfurization reaction, columns for a prefraction process are required in order to separate a C6 hydrocarbon and C7+ hydrocarbons therefrom, and the separated C7+ hydrocarbons are subjected to a dealkylation reaction and then mixed with the C6 hydrocarbon again, which makes the process complicated. In addition, even in the case in which the conventional benzene production process and the styrene extractive distillation process are theoretically combined, the raw material stream is supplied to the C7 separation column (DeC7) in the styrene extractive distillation processes and the upper discharge stream from the C7 separation column (DeC7) including C7-hydrocarbons is supplied to the first gasoline hydrogenation unit ($1^{st}$ GHT). Thus, a flow rate of the first gasoline hydrogenation unit ($1^{st}$ GHT) is increased and the C6 separation column (DeC6) for separating the C6 hydrocarbon and the C7+ hydrocarbons is required at a rear end of the first gasoline hydrogenation unit ($1^{st}$ GHT). Accordingly, the conventional process still requires an unnecessary process. However, in the present invention, the raw material stream is supplied to the C6 separation column (DeC6), and only the upper discharge stream including C6− hydrocarbons is supplied to the first gasoline hydrogenation unit (1$^{st}$ GHT), the lower discharge stream is supplied to the C7 separation column (DeC7), and the upper discharge stream including a C7 hydrocarbon is supplied to the hydrodealkylation reaction unit (HDA), respectively, thereby decreasing the flow rate supplied to the first gasoline hydrogenation unit (1$^{st}$ GHT) and also not requiring additional separation to reduce energy and utility costs.

According to an exemplary embodiment of the present invention, the raw material stream including C5 and C6 hydrocarbons may be separately supplied to the first gasoline hydrogenation unit (1$^{st}$ GHT). Here, the raw material stream supplied to the first gasoline hydrogenation unit (1$^{st}$ GHT) may not include styrene. For example, the raw material stream including C5 and C6 hydrocarbons separately supplied to the gasoline hydrogenation unit (1$^{st}$ GHT) may include one or more selected from the group consisting of cyclopentadiene, pentadiene, isoprene, cyclopentene, 1-pentene, 3-methyl-1-butene, cyclopentane, 2-methylbutene, normal pentane, benzene, and a C6 non-aromatic hydrocarbon, as the lower discharge stream from a C4 separation column (not shown) in an NCC process. Conventionally, the lower discharge stream from the C4 separation column was mixed with RPG described above and used as the raw material stream of a benzene production process and a styrene production process. However, the lower discharge stream from the C4 separation column includes benzene but does not include styrene, and thus, when supplied to the C6 separation column (DeC6), an additional process such as unnecessary separation and mixing is performed. Thus, in the present invention, the lower discharge stream from the C4 separation column (not shown) is separately supplied to the first gasoline hydrogenation unit (1$^{st}$ GHT) to decrease the flow rate supplied to the C6 separation column (DeC6) and avoid an unnecessary process step, so that energy may be reduced.

A content of olefins in the raw material stream separately supplied to the first gasoline hydrogenation unit (1$^{st}$ GHT) may be 40 wt % or more, 40 wt % to 70 wt %, or 40 wt % to 60 wt %.

According to an exemplary embodiment of the present invention, the stream discharged from the first gasoline hydrogenation unit (1$^{st}$ GHT) may include a C6 aromatic hydrocarbon. As a specific example, the discharge stream from the first gasoline hydrogenation unit (1$^{st}$ GHT) may be a stream abundant in benzene, which is supplied to the first extractive distillation column (1$^{st}$ EDC) and subjected to an extraction process, and then benzene may be separated.

In the first extractive distillation column (1$^{st}$ EDC), an extraction solvent may be used to separate and produce benzene from the discharge stream from the first gasoline hydrogenation unit (1$^{st}$ GHT). For example, the extraction solvent may include one or more selected from the group consisting of sulfolane, alkyl-sulfolane, N-formyl morpholine, N-methyl pyrrolidone, tetraethylene glycol, triethylene glycol, and diethylene glycol. In addition, the extraction solvent may further include water as a co-solvent.

In the first extractive distillation column (1$^{st}$ EDC), the extraction solvent may be used to separate an aromatic hydrocarbon and a non-aromatic (Non Aro) hydrocarbon in the discharge stream from the first gasoline hydrogenation unit (1$^{st}$ GHT). Specifically, in the first extractive distillation column (1$^{st}$ EDC), an aromatic hydrocarbon in the discharge stream from the first gasoline hydrogenation unit (1$^{st}$ GHT) may be selectively extracted and discharged to the lower portion of the first extractive distillation column (1$^{st}$ EDC), and a non-aromatic hydrocarbon may be separated from the upper portion of the first extractive distillation column (1$^{st}$ EDC).

A separately required device may be further included at a rear end of the first extractive distillation column (1$^{st}$ EDC). For example, the lower discharge stream from the first extractive distillation column (1$^{st}$ EDC) may include the extraction solvent together with the aromatic hydrocarbons as an extract. Therefore, the lower discharge stream from the first extractive distillation column (1$^{st}$ EDC) may pass through a separate solvent recovery column to be separated into the extraction solvent and the aromatic hydrocarbons.

According to an exemplary embodiment of the present invention, the upper discharge stream from the C7 separation column (DeC7) may be supplied to the hydrodealkylation reaction unit (HDA) to be subjected to a dealkylation reaction. The upper discharge stream from the C7 separation column (DeC7) may include a C7 aromatic hydrocarbon. The C7 aromatic hydrocarbon in the upper discharge stream from the C7 separation column (DeC7) supplied to the hydrodealkylation reaction unit (HDA) may be subjected to a dealkylation reaction to produce benzene. The dealkylation reaction is a reaction where hydrogen is added to aromatic hydrocarbons including an alkyl group to release the alkyl group from a benzene ring. In addition, a hydrodesulfurization reaction occurs together with the dealkylation reaction in the hydrodealkylation reaction unit (HDA), and an unsaturated hydrocarbon may be converted into a saturated hydrocarbon. Here, the upper discharge stream from the C7 separation column (DeC7) is a stream abundant in toluene, and may be subjected to the dealkylation reaction to release an alkyl group bonded to a benzene ring of the toluene, thereby producing benzene. Here, the discharge stream from the hydrodealkylation reaction unit (HDA) is a stream abundant in benzene, and benzene may be separated therefrom.

The lower discharge stream from the first extractive distillation column (1$^{st}$ EDC), for example, the lower discharge stream from the first extractive distillation column (1$^{st}$ EDC) including an aromatic hydrocarbon separated through a solvent recovery column and the discharge stream from the hydrodealkylation reaction unit (HDA) may pass through one or more benzene separation columns (BZ), thereby separating benzene from the lower discharge stream from the first extractive distillation column (1$^{st}$ EDC) and the discharge stream from the hydrodealkylation reaction unit (HDA). In addition, the lower discharge stream from the benzene separation column (BZ) includes a trace amount of C7+ hydrocarbons, and a toluene separation column (TOL) for separating a C7 hydrocarbon therefrom may be further provided. In TOL, the upper discharge stream including a C7 hydrocarbon is supplied to the hydrodealkylation reaction unit (HDA) and C8+ hydrocarbon heavy materials may be discharged from the lower portion. Here, the lower discharge stream from the first extractive distillation column (1$^{st}$ EDC) and the discharge stream from the hydrodealkylation reaction unit (HDA) may be supplied to the benzene separation column (BZ) as individual streams, or may be supplied to the benzene separation column (BZ) as a mixed stream.

According to an exemplary embodiment of the present invention, the lower discharge stream from the C7 separation column (DeC7) may be supplied to the C8 separation column (DeC8) as a stream including C8+ hydrocarbons, and in the C8 separation column (DeC8), may be separated into an upper discharge stream including a C8 hydrocarbon and a lower discharge stream including C9+ hydrocarbons.

Here, the stream including C9+ hydrocarbons may be removed by being discharged to the outside through the lower discharge stream from the C8 separation column (DeC8) to remove an unnecessary process in which components which are not required in the BTX production process are hydrodesulfurized and removed after separation.

According to an exemplary embodiment of the present invention, the upper discharge stream from the C8 separation column (DeC8) including C8 hydrocarbons may be supplied to the second extractive distillation column ($2^{nd}$ EDC) and subjected to an extraction process.

In the second extractive distillation column ($2^{nd}$ EDC), aromatic hydrocarbons and vinyl aromatic hydrocarbons may be separated from the upper discharge stream from the C8 separation column (DeC8) using the extraction solvent. Specifically, in the second extractive distillation column ($2^{nd}$ EDC), the C8 vinyl aromatic hydrocarbon abundant in styrene in the upper discharge stream from the C8 separation column (DeC8) may be selectively extracted to be separated as the lower portion of the second extractive distillation column ($2^{nd}$ EDC), and the C8 aromatic hydrocarbon abundant in xylene may be separated from the upper portion of the second extractive distillation column ($2^{nd}$ EDC). Here, the extraction solvent may include, for example, one or more selected from the group consisting of for example, sulfolane, alkyl-sulfolane, N-formyl morpholine, N-methyl pyrrolidone, tetraethylene glycol, triethylene glycol, and diethylene glycol. In addition, the extraction solvent may further include water as a co-solvent.

The second extractive distillation column ($2^{nd}$ EDC) may separate styrene from the lower discharge stream, and xylene may be separated from the upper discharge stream from the second extractive distillation column ($2^{nd}$ EDC), respectively.

A separately required device may be further included at the rear end of the second extractive distillation column ($2^{nd}$ EDC). For example, the lower discharge stream from the second extractive distillation column ($2^{nd}$ EDC) may include the extraction solvent together with the C8 vinyl aromatic hydrocarbon as an extract. Therefore, the lower discharge stream from the second extractive distillation column ($2^{nd}$ EDC) may pass through a separate solvent recovery column to be separated into the extraction solvent and the C8 vinyl aromatic hydrocarbon, thereby separating the C8 vinyl aromatic hydrocarbon, that is, styrene.

The upper discharge stream from the second extractive distillation column ($2^{nd}$ EDC) is a stream including a C8 aromatic hydrocarbon abundant in xylene, and may pass through the second gasoline hydrogenation unit ($2^{nd}$ GHT) to produce xylene. Specifically, in the second gasoline hydrogenation unit ($2^{nd}$ GHT), olefins and sulfur remaining in the upper discharge stream from the second extractive distillation column ($2^{nd}$ EDC) may be hydrogenated and removed, and xylene (MX) may be directly produced from the upper discharge stream of the second extractive distillation column ($2^{nd}$ EDC) which has passed through the second gasoline hydrogenation unit ($2^{nd}$ GHT).

Hydrogen and a catalyst are separately supplied to the second gasoline hydrogenation unit ($2^{nd}$ GHT), and a gasoline hydrogenation process of hydrodesulfurization in the presence of hydrogen and the catalyst may be performed. The catalyst may be a catalyst allowing selective hydrogenation. For example, the catalyst may include one or more selected from the group consisting of palladium, platinum, copper, and nickel. In some cases, the catalyst may be supported on one or more supporters selected from the group consisting of gamma alumina, activated carbon, and zeolite.

Unlike the first gasoline hydrogenation unit ($1^{st}$ GHT), the second gasoline hydrogenation unit ($2^{nd}$ GHT) does not include the two gasoline hydrogenation reactors and includes only a third gasoline hydrogenation reactor, thereby decreasing a plant size and minimizing energy use. Specifically, the upper discharge stream from the second extractive distillation column ($2^{nd}$ EDC) supplied to the third gasoline hydrogenation reactor includes a C8 aromatic hydrocarbon abundant in xylene and hardly contains olefins such as diolefin and styrene, thereby omitting a hydrogenation reaction to remove olefins by a liquid phase reaction at a low temperature. For example, the content of the olefins contained in the upper discharge stream from the second extractive distillation column ($2^{nd}$ EDC) may be 0.1 wt % or less or 0.01 wt % to 0.1 wt %.

Specifically, the upper discharge stream from the second extractive distillation column ($2^{nd}$ EDC) is supplied to the third gasoline hydrogenation reactor, and the hydrogenation reaction may be carried out in the third gasoline hydrogenation reactor at a temperature of 250° C. to 400° C., 280° C. to 360° C., or 280° C. to 320° C. The third gasoline hydrogenation reactor is operated at the temperature in the above ranges, thereby performing the hydrogenation reaction in a gas phase. Specifically, in the third gasoline hydrogenation reactor, the olefins remaining in the upper discharge stream from the second extractive distillation column ($2^{nd}$ EDC) are removed, and the hydrogenation reaction may be performed in a gaseous phase to remove sulfur. Thus, a C8 aromatic hydrocarbon abundant in xylene from which olefins and sulfur are removed is discharged from the third gasoline hydrogenation reactor, and xylene (MX) may be produced without additional separation from the discharge stream of the third gasoline hydrogenation reactor.

However, even in the case in which the conventional benzene production process and styrene extractive distillation process are theoretically combined, the stream including a C8 aromatic hydrocarbon separated from the styrene extractive distillation process, that is, the upper discharge stream from the second extractive distillation column ($2^{nd}$ EDC), will be supplied to the first gasoline hydrogenation unit ($1^{st}$ GHT) together with the upper discharge stream from the C7 separation column (DeC7) as the raw material of the benzene production process.

When the upper discharge stream from the second extractive distillation column ($2^{nd}$ EDC) is supplied to the first gasoline hydrogenation unit ($1^{st}$ GHT) as a raw material of the benzene production process together with the upper discharge stream from the C7 separation column (DeC7), the amount of hydrogen used increases and a catalyst lifetime decreases because of an increase in a flow rate supplied to the first gasoline hydrogenation unit ($1^{st}$ GHT). In addition, although the upper discharge stream from the second extractive distillation column ($2^{nd}$ EDC) includes a very small amount of olefins, the stream passes through both the first gasoline hydrogenation reactor and the second gasoline hydrogenation reactor like the first gasoline hydrogenation unit ($1^{st}$ GHT), resulting in unnecessary energy use. In addition, since the stream discharged from the first gasoline hydrogenation unit ($1^{st}$ GHT) also includes a C8 aromatic hydrocarbon together with a C6 aromatic hydrocarbon and a C7 aromatic hydrocarbon, a plurality of separation columns for separating them are required at a rear end of the discharge stream from the first gasoline hydrogenation unit ($1^{st}$ GHT) and the stream passes through the hydrodealkylation reaction unit (HDA) again.

In addition, more similarly to the present application, even in the case in which the conventional benzene production process and the styrene extractive distillation process is theoretically combined and designed, the upper discharge stream from the second extractive distillation column ($2^{nd}$ EDC) will be supplied to the hydrodealkylation reaction unit (HDA) together with the upper discharge stream from the C7 separation column (DeC7).

When the upper discharge stream from the second extractive distillation column ($2^{nd}$ EDC) is supplied to the hydrodealkylation reaction unit (HDA) together with the upper discharge stream from the C7 separation column (DeC7), benzene may be further produced, but because the stream is subjected to a step of mixing with the upper discharge stream from the C7 separation column (DeC7), a step of performing a dealkylation reaction, a step of mixing with the upper discharge stream from the first extractive distillation column ($1^{st}$ EDC), and a step of benzene separation, the path becomes longer and complicated, and xylene may not be produced.

According to an exemplary embodiment of the present invention, if necessary, devices such as a distillation column (not shown), a condenser (not shown), a reboiler (not shown), a valve (not shown), a pump (not shown), a separator (not shown), and a mixer (not shown) may be further installed in the method of producing aromatic hydrocarbons.

Hereinabove, the method of producing aromatic hydrocarbons according to the present invention has been described and illustrated in the drawings, but of the drawings illustrate only core components for understanding the present invention, and in addition to the process and apparatus described above and illustrated in the drawings, the process and the apparatus which are not described and illustrated separately may be appropriately applied and used for carrying out the method of producing aromatic hydrocarbons according to the present invention.

Hereinafter, the present invention will be described in more detail according to the Examples. However, the Examples are provided for illustrating the present invention. It would be apparent to a person skilled in the art that various modifications and alterations may be made without departing from the scope and spirit of the present invention, and the scope of the present invention is not limited thereto.

EXAMPLES

Example 1

The process illustrated in FIG. 1 was simulated using an Aspen Plus simulator from Aspen Technology, Inc.

Specifically, a raw material stream including C5 to C10 hydrocarbons was supplied to a C6 separation column (DeC6) and a raw material stream including C5 and C6 hydrocarbons but no styrene was supplied to a first gasoline hydrogenation unit ($1^{st}$ GHT).

An upper discharge stream from the C6 separation column (DeC6) including C6− hydrocarbons was supplied to the first gasoline hydrogenation unit ($1^{st}$ GHT), and a lower discharge stream from the C6 separation column (DeC6) including C7+ hydrocarbons was supplied to a C7 separation column (DeC7). In addition, in the C7 separation column (DeC7), an upper discharge stream including a C7 hydrocarbon was supplied to the hydrodealkylation reaction unit (HDA), and a lower discharge stream including C8+ hydrocarbons was supplied to the C8 separation column (DeC8).

The upper discharge stream from the C6 separation column (DeC6) including C6− hydrocarbons was supplied to the first gasoline hydrogenation unit ($1^{st}$ GHT), and a total amount of the discharge stream from the first gasoline hydrogenation unit ($1^{st}$ GHT) including the C6 aromatic hydrocarbon was supplied to the first extractive distillation column ($1^{st}$ EDC).

The lower discharge stream from the first extractive distillation column ($1^{st}$ EDC) included the C6 aromatic hydrocarbons, but was a stream from which non-aromatic hydrocarbons were removed, and was supplied to the benzene separation column (BZ) with the discharge stream from the hydrodealkylation reaction unit (HDA), and benzene was separated from an upper portion of the benzene separation column (BZ) and the lower discharge stream was supplied to the toluene separation column (TOL). In the toluene separation column (TOL), the C7 aromatic hydrocarbon was separated from the upper portion and supplied to the hydrodealkylation reaction unit (HDA), and a heavy substance including the C8+ hydrocarbons was separated from the lower portion and removed.

The lower discharge stream from the C7 separation column (DeC7) including C8+ hydrocarbons was supplied to the C8 separation column (DeC8), and the lower discharge stream from the C8 separation column (DeC8) including C9+ hydrocarbons was discharged to the outside and removed, and the upper discharge stream from the C8 separation column (DeC8) including a C8 hydrocarbon was supplied to a second extractive distillation column ($2^{nd}$ EDC).

The lower discharge stream from the second extractive distillation column ($2^{nd}$ EDC) included styrene and was supplied to a solvent recovery column to remove a solvent and then styrene was separated.

In addition, the upper discharge stream from the second extractive distillation column ($2^{nd}$ EDC) was a stream abundant in xylene and was supplied to the second gasoline hydrogenation unit ($2^{nd}$ GHT), and xylene was produced from the discharge stream from the second gasoline hydrogenation unit ($2^{nd}$ GHT).

A flow rate (ton/hr) of the streams S1, S2, S11, S12, S13, S21, S22, S23, S24, S25, S26, S27, S28, S41 in FIG. 1 depending on a process flow of the process simulation is shown in Table 1. In addition, a total amount of steam used in the process was measured as a total amount of energy used in the process, and is shown in Table 2, as a criterion (100.0) for a total amount of steam used in the other Examples and Comparative Examples.

Example 2

The process was performed in the same manner as in Example 1, except that the raw material stream including C5 and C6 hydrocarbons but no styrene was supplied to not the first gasoline hydrogenation unit ($1^{st}$ GHT) but the C6 separation column (DeC6).

A flow rate (ton/hr) of the streams S2, S11, S12, S13, S21, S22, S23, S24, S25, S26, S27, S28, S41 in FIG. 1 depending on a process flow of the process simulation is shown in Table 1. In addition, a total amount of steam used in the process was measured as a total amount of energy used in the process relative to the amount of steam used in Example 1, and is shown in Table 2.

COMPARATIVE EXAMPLE

Comparative Example 1

For the process illustrated in FIG. 2 was simulated using an Aspen Plus simulator from Aspen Technology, Inc.

Specifically, a raw material stream including C5 to C10 hydrocarbons as the raw material stream was supplied to the first gasoline hydrogenation unit ($1^{st}$ GHT) and the discharge stream from the first gasoline hydrogenation unit ($1^{st}$ GHT) was supplied to the C6 separation column (DeC6). In the C6 separation column (DeC6), the upper discharge stream including a C6 aromatic hydrocarbon was supplied to the first extractive distillation column ($1^{st}$ EDC), and the lower discharge stream including C7+ aromatic hydrocarbons was supplied to a C9 separation column (DeC9).

In the C9 separation column (DeC9), C8+ hydrocarbons were discharged to the lower portion and the stream including C7 and C8 aromatic hydrocarbons was supplied to the hydrodealkylation reaction unit (HDA).

A lower discharge stream from the first extractive distillation column ($1^{st}$ EDC) and a discharge stream from the hydrodealkylation reaction unit (HDA) were mixed and passed through the benzene separation column (BZ) to separate benzene, and the lower discharge stream from the benzene separation column (BZ) was supplied to the toluene separation column (TOL). In the toluene separation column (TOL), the C7 aromatic hydrocarbon was separated from the upper portion and supplied to the hydrodealkylation reaction unit (HDA), and a heavy substance including the C8+ hydrocarbons was separated from the lower portion and removed.

A flow rate (ton/hr) of the streams S1, S11, S12, S13, S30, S31, S32, S33 in FIG. 2 depending on a process flow of the process simulation is shown in Table 1.

Comparative Example 2

The process illustrated in FIG. 3 was simulated using an Aspen Plus simulator from Aspen Technology, Inc.

Specifically, a raw material stream including C5 to C10 hydrocarbons was supplied to the C7 separation column (DeC7) and a raw material stream including C5 and C6 hydrocarbons but no styrene was supplied to the first gasoline hydrogenation unit ($1^{st}$ GHT).

An upper discharge stream from the C7 separation column (DeC7) including C7− hydrocarbons was supplied to the first gasoline hydrogenation unit ($1^{st}$ GHT), and a lower discharge stream from the C7 separation column (DeC7) including C8+ hydrocarbons was supplied to the C8 separation column (DeC8).

In the C8 separation column (DeC8), the upper discharge stream from which C9+ hydrocarbons were removed was supplied to the second extractive distillation column ($2^{nd}$ EDC). The stream including styrene was separated from the lower discharge stream from the second extractive distillation column ($2^{nd}$ EDC) and supplied to the solvent recovery column to remove a solvent, and styrene was separated. In addition, the upper discharge stream from the second extractive distillation column ($2^{nd}$ EDC) was a stream including xylene and was supplied to the first gasoline hydrogenation unit ($1^{st}$ GHT) together with the upper discharge stream from the C7 separation column (DeC7).

The discharge stream from the first gasoline hydrogenation unit ($1^{st}$ GHT) included C6 to C8 aromatic hydrocarbons and was supplied to the C6 separation column (DeC6). In the C6 separation column (DeC6), the stream was separated into an upper discharge stream including a C6 aromatic hydrocarbon and a lower discharge stream including C7+ aromatic hydrocarbons, and the upper discharge stream was supplied to the first extractive distillation column ($1^{st}$ EDC) and the lower discharge stream was supplied to the hydrodealkylation reaction unit (HDA).

The lower discharge stream from the first extractive distillation column ($1^{st}$ EDC) was mixed with the discharge stream from the hydrodealkylation reaction unit (HDA) and passed through the benzene separation column (BZ) to separate benzene, and the lower discharge stream from the benzene separation column (BZ) was supplied to the toluene separation column (TOL). In the toluene separation column (TOL), the C7 aromatic hydrocarbon was separated from the upper portion and supplied to the hydrodealkylation reaction unit (HDA), and a heavy substance including the C8+ hydrocarbons was separated from the lower portion and removed.

A flow rate (ton/hr) of the streams S1, S2, S11, S12, S13, S23, S24, S25, S26, S30, S31, S40, S41 in FIG. 3 depending on a process flow of the process simulation is shown in Table 1.

Comparative Example 3

The process illustrated in FIG. 4 was simulated using an Aspen Plus simulator from Aspen Technology, Inc.

Specifically, a raw material stream including C5 to C10 hydrocarbons was supplied to the C7 separation column (DeC7) and a raw material stream including C5 and C6 hydrocarbons but no styrene was supplied to the first gasoline hydrogenation unit ($1^{st}$ GHT).

An upper discharge stream from the C7 separation column (DeC7) including C7− hydrocarbons was supplied to the first gasoline hydrogenation unit ($1^{st}$ GHT), and a lower discharge stream from the C7 separation column (DeC7) including C8+ hydrocarbons was supplied to the C8 separation column (DeC8).

In the C8 separation column (DeC8), the upper discharge stream from which C9+ hydrocarbons were removed was supplied to the second extractive distillation column ($2^{nd}$ EDC). The stream including styrene was separated from the lower discharge stream from the second extractive distillation column ($2^{nd}$ EDC) and supplied to the solvent recovery column to remove a solvent, and styrene was separated. In addition, the upper discharge stream from the second extractive distillation column ($2^{nd}$ EDC) was a stream including xylene and was supplied to the first gasoline hydrogenation unit ($1^{st}$ GHT) together with the upper discharge stream from the C7 separation column (DeC7).

The discharge stream from the first gasoline hydrogenation unit ($1^{st}$ GHT) included C6 to C8 aromatic hydrocarbons and was supplied to the C6 separation column (DeC6). In the C6 separation column (DeC6), the stream was separated into an upper discharge stream including a C6 aromatic hydrocarbon and a lower discharge stream including C7 and C8 aromatic hydrocarbons, and the upper discharge stream was supplied to the first extractive distillation column ($1^{st}$ EDC) and the lower discharge stream was supplied to the xylene separation column (MX).

In the xylene separation column (MX), xylene was separated from the lower discharge stream, and the upper discharge stream was supplied to the hydrodealkylation reaction unit (HDA) to perform a dealkylation reaction.

The lower discharge stream from the first extractive distillation column ($1^{st}$ EDC) was mixed with the discharge stream from the hydrodealkylation reaction unit (HDA) and passed through the benzene separation column (BZ) to separate benzene, and the lower discharge stream from the benzene separation column (BZ) was supplied to the toluene separation column (TOL). In the toluene separation column (TOL), the C7 aromatic hydrocarbon was separated from the upper portion and supplied to the hydrodealkylation reaction unit (HDA), and a heavy substance including the C8+ hydrocarbons was separated from the lower portion and removed.

A flow rate (ton/hr) of the streams S1, S2, S11, S12, S13, S23, S24, S25, S26, S30, S31, S32, S33, S40, S41 in FIG. 4 depending on a process flow of the process simulation is shown in Table 1. In addition, a total amount of steam used in the process was measured as a total amount of energy used in the process relative to the amount of steam used in Example 1, and is shown in Table 2.

TABLE 1

| | Example 1 | Example 2 | Comparative Example 1 | Comparative Example 2 | Comparative Example 3 |
|---|---|---|---|---|---|
| S1 | 20.4 | N/A | 176.4 | 20.4 | 20.4 |
| S2 | 156 | 176.4 | N/A | 156 | 156 |
| S11 | 74.3 | 74.3 | 86.2 | 74.3 | 74.3 |
| S12 | 75.4 | 75.4 | 89.4 | 83.2 | 75.4 |
| S13 | 61 | 61 | 68.8 | 68.2 | 61 |
| S21 | 88.6 | 109 | N/A | N/A | N/A |
| S22 | 67.4 | 67.4 | N/A | N/A | N/A |
| S23 | 22.6 | 22.6 | N/A | 111.2 | 111.2 |
| S24 | 44.8 | 44.8 | N/A | 44.8 | 44.8 |
| S25 | 20.4 | 20.4 | N/A | 20.4 | 20.4 |
| S26 | 10.3 | 10.3 | N/A | 10.3 | 10.3 |
| S27 | 10.1 | 10.1 | N/A | N/A | N/A |
| S28 | 10.1 | 10.1 | N/A | N/A | N/A |
| S30 | N/A | N/A | 144 | 109.4 | 109.4 |
| S31 | N/A | N/A | 57.8 | 35.2 | 35.2 |
| S32 | N/A | N/A | 20.4 | N/A | 25.2 |
| S33 | N/A | N/A | 37.4 | N/A | 10.1 |
| S40 | N/A | N/A | N/A | 10.1 | 10.1 |
| S41 | 24.4 | 24.4 | N/A | 24.4 | 24.4 |

TABLE 2

| | Example 1 | Example 2 | Comparative Example 3 |
|---|---|---|---|
| Total amount of steam used | 100.0 | 105.7 | 118.7 |

* Total amount of steam used: Ratio of the total amount of steam used relative to a criterion (Example 1: 100.0)

Referring to Tables 1 and 2, in Examples 1 and 2 in which xylene, as well as benzene and styrene, was produced according to the method according to the present invention, total output of aromatic hydrocarbons was at an equal or superior level to that of the Comparative Examples.

In particular, the total amount of steam used for heating in the process of Example 1 was the lowest among in the processes of Examples 1 to 3. Specifically, in Example 1, the flow rate supplied to the C6 separation column (DeC6) may be decreased to decrease the amount of steam used in the C6 separation column (DeC6) because the raw material stream including C5 and C6 hydrocarbons but no styrene was not supplied to the C6 separation column (DeC6) but separately supplied to the first gasoline hydrogenation unit ($1^{st}$ GHT). In addition, the upper discharge stream from the C7 separation column (DeC7) was not supplied to the first gasoline hydrogenation unit ($1^{st}$ GHT) together with the upper discharge stream from the C6 separation column (DeC6) but separately supplied to the hydrodealkylation reaction unit (HDA), and the upper discharge stream from the second extractive distillation column ($2^{nd}$ EDC) was not supplied to the first gasoline hydrogenation unit ($1^{st}$ GHT) or the hydrodealkylation reaction unit (HDA) to perform unnecessary separation, mixing, and complicated hydrogenation reaction but supplied to a separate second gasoline hydrogenation unit ($2^{nd}$ GHT) to produce xylene, thereby minimizing the amount of energy used while further producing xylene as well as benzene and styrene. In addition, in Example 2, the stream supplied to the C6 separation column (DeC6) was increased, so that the amount of steam used was somewhat increased compared to that in Example 1.

In comparison, a comparison data for the total amount of steam used was not added for Comparative Example 1 because the process of Comparative Example 1 did not produce styrene and xylene and only produced benzene and, thus, was not a comparison target. However, since the stream supplied to the first gasoline hydrogenation unit ($1^{st}$ GHT) was 176.4 ton/hr which was the largest amount, the amount of hydrogen used in the first gasoline hydrogenation unit ($1^{st}$ GHT) was significant and the catalyst lifetime was decreased, thereby increasing utility costs.

In addition, Comparative Example 2 was a theoretical combination of a benzene production process and a styrene production process and did not include production of xylene, and a comparison data for the total amount of steam used was not added. However, unlike the Examples in which the upper discharge stream from the C7 separation column (DeC7) including a C7 hydrocarbon was supplied to the first gasoline hydrogenation unit ($1^{st}$ GHT) and the upper discharge stream separated from the second extractive distillation column ($2^{nd}$ EDC) was used to produce xylene, in Comparative Example 2, the upper discharge stream from the second extractive distillation column ($2^{nd}$ EDC) including a C8 hydrocarbon was input to the first gasoline hydrogenation unit ($1^{st}$ GHT), thereby increasing the stream supplied to the first gasoline hydrogenation unit ($1^{st}$ GHT) to increase the amount of hydrogen used, decrease a catalyst lifetime, and increase utility costs. In addition, since C7 and C8 hydrocarbons were introduced to the benzene production process, the C6 separation column (DeC6) for prefraction in the benzene production process was not removed, the amount of steam used was increased, and the stream supplied to the hydrodealkylation reaction unit (HDA) was increased to increase the amount of hydrogen used required in the hydrodealkylation reaction unit (HDA).

In addition, in Comparative Example 3, the benzene production process and the styrene production process were theoretically combined and modified into a process that also produced styrene. Comparative Example 3 had the same problems as Comparative Example 2. In addition, it was found that the xylene separation column (MX) was further placed in the lower portion of the C6 separation column (DeC6) to separate xylene, thereby unnecessarily subjecting C7 and C8 hydrocarbons to separation, mixing, and reseparation processes to increase the amount of energy used and decrease the total output of benzene, styrene, and xylene.

The invention claimed is:

1. A method of producing aromatic hydrocarbons, the method comprising:
   a step of supplying a first raw material stream to a C6 separation column, supplying an upper discharge stream from the C6 separation column to a first gasoline hydrogenation unit, and supplying a lower discharge stream from the C6 separation column to a C7 separation column;
   a step of supplying an upper discharge stream from the C7 separation column to a hydrodealkylation reaction unit and supplying a lower discharge stream from the C7 separation column to a C8 separation column;
   a step of separating benzene from a discharge stream of the first gasoline hydrogenation unit and a discharge stream of the hydrodealkylation reaction unit;

a step of removing a lower discharge stream from the C8 separation column and supplying an upper discharge stream from the C8 separation column to a second extractive distillation column; and a step of separating styrene from a lower discharge stream of the second extractive distillation column and separating xylene from an upper discharge stream of the second extractive distillation column, wherein the first gasoline hydrogenation unit is separately supplied with a second raw material stream including a C5 hydrocarbon and a C6 hydrocarbon, wherein the second raw material stream supplied to the first gasoline hydrogenation unit is different from the first raw material stream and does not include styrene; and wherein the first raw material stream includes C5 to C10 hydrocarbons.

2. The method of producing aromatic hydrocarbons of claim 1, wherein in the step of separating benzene, the discharge stream from the first gasoline hydrogenation unit is supplied to a first extractive distillation column, and benzene is separated from a lower discharge stream of the first extractive distillation column.

3. The method of producing aromatic hydrocarbons of claim 2, wherein the lower discharge stream from the first extractive distillation column and the discharge stream from the hydrodealkylation reaction unit form a mixed stream, and benzene is separated from the mixed stream.

4. The method of producing aromatic hydrocarbons of claim 1, wherein in the step of separating xylene, the upper discharge stream of the second extractive distillation column is supplied to a second gasoline hydrogenation unit, and xylene is separated from a discharge stream of the second gasoline hydrogenation unit.

5. The method of producing aromatic hydrocarbons of claim 4, wherein the second gasoline hydrogenation unit includes a gasoline hydrogenation reactor, and wherein an operation temperature of the gasoline hydrogenation reactor is 250° C. to 350° C.

6. The method of producing aromatic hydrocarbons of claim 1, wherein the lower discharge stream from the C8 separation column includes C9+ hydrocarbons.

* * * * *